United States Patent
Lin et al.

(10) Patent No.: US 11,938,157 B2
(45) Date of Patent: Mar. 26, 2024

(54) *LACTOBACILLUS PARACASEI* TCI727 AND METHOD FOR PROMOTING CALCIUM ABSORPTION BY USING *LACTOBACILLUS PARACASEI* TCI727/OR ITS METABOLITES

(71) Applicant: TCI CO., LTD., Taipei (TW)

(72) Inventors: Yung-Hsiang Lin, Taipei (TW); Chu-Han Huang, Taipei (TW)

(73) Assignee: TCI CO., LTD., Taipei (TW)

( * ) Notice: Subject to any disclaimer, the term of this patent is extended or adjusted under 35 U.S.C. 154(b) by 0 days.

(21) Appl. No.: 17/812,182

(22) Filed: Jul. 13, 2022

(65) Prior Publication Data

US 2023/0029084 A1 Jan. 26, 2023

Related U.S. Application Data

(60) Provisional application No. 63/221,010, filed on Jul. 13, 2021.

(51) Int. Cl.

| | | |
|---|---|---|
| *A61K 35/747* | (2015.01) | |
| *A61K 8/9789* | (2017.01) | |
| *A61K 36/746* | (2006.01) | |
| *A61P 3/04* | (2006.01) | |
| *A61P 17/16* | (2006.01) | |
| *A61P 17/18* | (2006.01) | |
| *A61P 19/08* | (2006.01) | |
| *A61Q 19/00* | (2006.01) | |
| *C12N 1/20* | (2006.01) | |
| *C12N 9/16* | (2006.01) | |
| *C12R 1/225* | (2006.01) | |

(52) U.S. Cl.
CPC ............ *A61K 35/747* (2013.01); *A61P 19/08* (2018.01); *C12N 1/205* (2021.05); *C12N 9/16* (2013.01); *C12R 2001/225* (2021.05)

(58) Field of Classification Search
CPC ....... A61K 35/747; A61P 19/08; C12N 1/205; C12N 9/16; C12R 2001/225
See application file for complete search history.

(56) References Cited

U.S. PATENT DOCUMENTS

| | | | |
|---|---|---|---|
| 2005/0019894 A1* | 1/2005 | Park | A23L 5/28 426/43 |
| 2019/0321420 A1* | 10/2019 | Chen | A23L 33/135 |
| 2021/0113633 A1* | 4/2021 | Ohlsson | A61K 31/593 |

FOREIGN PATENT DOCUMENTS

WO     2013102430 A1     7/2013

OTHER PUBLICATIONS

Bhagat et. al. (Production of phytase from Lactobacillus paracasei strain and its probiotic profile, Indian Journal of Experimental Biology, Nov. 2019) (Year: 2019).*
Dubey et. al. (Probiotics: A Promising Tool for Calcium Absorption, The Open Nutrition Journal, Aug. 2018) (Year: 2018).*
Examination report dated Dec. 6, 2023, listed in correspondent Taiwan patent application No. 111126328 (Publication No. 202302837).
Deepali Bhagat, et al., Production of phytase from Lactobacillus paracasei strain and its probiotic profile, Indian Journal of Experimental Biology, vol. 57, Nov. 2019, pp. 839-851. Full text.

* cited by examiner

*Primary Examiner* — Suzanne M Noakes
*Assistant Examiner* — Jae W Lee
(74) *Attorney, Agent, or Firm* — Chich-Mei Wang

(57) ABSTRACT

Provided is *Lactobacillus paracasei* TCI727, deposited in the Deutsche Sammlung von Mikroorganismen und Zellkulturen GmbH (DSMZ) with a deposit number of DSM 33756. A method for improving calcium absorption of a subject in need thereof by using the *Lactobacillus paracasei* TCI727 or metabolites thereof is also provided. The method includes administering to the subject an effective amount of a composition comprising the *Lactobacillus paracasei* TCI727 or the metabolites thereof.

9 Claims, 4 Drawing Sheets

Specification includes a Sequence Listing.

LACTOBACILLUS PARACASEI TCI727 AND METHOD FOR PROMOTING CALCIUM ABSORPTION BY USING LACTOBACILLUS PARACASEI TCI727/OR ITS METABOLITES

CROSS-REFERENCE TO RELATED APPLICATION

This application claims the benefit of U.S. provisional application Ser. No. 63/221,010, filed on Jul. 13, 2021. The entirety of the above-mentioned patent application is hereby incorporated by reference herein and made a part of the specification.

REFERENCE OF AN ELECTRONIC SEQUENCE LISTING

The contents of the electronic sequence listing (P212223USI_ST26.xml; Size: 9 KB; and Date of Creation: Jul. 13, 2022) is herein incorporated by reference in its entirety.

BACKGROUND

Technical Field

The present disclosure relates to a species of *Lactobacillus paracasei*, and in particular, to *Lactobacillus paracasei* TCI727 and a method for promoting calcium absorption by using *Lactobacillus paracasei* TCI727 or metabolites thereof.

Related Art

It was found from research that calcium absorption is easily inhibited by phytic acid. Foods rich in phytic acid include beans, grains, seeds, and nuts. In the intestinal tract, phytic acid will combine with calcium to form calcium salts, resulting in the calcium from consumed foods being excreted along with the phytic acid, which is not conducive to the absorption of calcium from consumed foods by an individual, and reduces the utilization rate of calcium absorbed by an individual. Therefore, although soybeans and sesame are rich in calcium, they are not good sources for calcium supplementation because they are rich in phytic acid themselves.

Due to the lack of phytase, the human body needs to rely on gut microbiota to facilitate the degradation of phytic acid in foods.

In addition, active transport of calcium has to be regulated by activated vitamin D to increase cellular calcium ion channel proteins, so as to promote the absorption of calcium.

SUMMARY

In view of this, in some embodiments, a species of *Lactobacillus paracasei* is provided, deposited in the Food Industry Research and Development Institute (with a deposit number of BCRC 911032) and the Deutsche Sammlung von Mikroorganismen und Zellkulturen GmbH (DSMZ) (with a deposit number of DSM 33756).

In some embodiments, the *Lactobacillus paracasei* TCI727 includes the nucleotide sequence as set forth in SEQ ID NO: 1.

In some embodiments, the *Lactobacillus paracasei* TCI727 includes a phytase.

In some other embodiments, provided is use of *Lactobacillus paracasei* TCI727 or metabolites thereof in preparing a composition for promoting calcium absorption. The *Lactobacillus paracasei* TCI727 is deposited in the Food Industry Research and Development Institute with a deposit number of BCRC 911032.

In some other embodiments, a method for improving calcium absorption of a subject in need thereof by using the *Lactobacillus paracasei* TCI727 or the metabolites thereof is provided, including administering to the subject an effective amount of a composition comprising the *Lactobacillus paracasei* TCI727 or the metabolites thereof. The *Lactobacillus paracasei* TCI727 is deposited in the Food Industry Research and Development Institute with a deposit number of BCRC 911032.

In some embodiments, the *Lactobacillus paracasei* TCI727 or the metabolites thereof are used to provide an effective amount of phytase to a subject.

In some embodiments, the *Lactobacillus paracasei* TCI727 or the metabolites thereof are used to increase the vitamin D level in a subject.

In some embodiments, the *Lactobacillus paracasei* TCI727 or the metabolites thereof are used to increase the content of calcium in bone cells.

In some embodiments, the *Lactobacillus paracasei* TCI727 or the metabolites thereof are used to increase the content of osteocalcin in a subject.

In some embodiments, the *Lactobacillus paracasei* TCI727 or the metabolites thereof are used to promote calcium absorption and/or osteogenesis of a subject.

In some embodiments, an effective amount of the *Lactobacillus paracasei* TCI727 in the composition is at least $1 \times 10^8$ CFU/day.

In some embodiments, the composition containing the *Lactobacillus paracasei* TCI727 or the metabolites thereof for promoting calcium absorption is in a dosage form of powder, granule, tablet, liquid, or colloid.

In some embodiments, when the composition is in the dosage form of powder, a dose of the *Lactobacillus paracasei* TCI727 or the metabolites thereof is 100 mg/day.

In some embodiments, the composition containing the *Lactobacillus paracasei* TCI727 or the metabolites thereof for promoting calcium absorption may be made into a food, drink, nutritional supplement, or medicament.

Based on the above, according to the *Lactobacillus paracasei* in any embodiment and the use of the *Lactobacillus paracasei* TCI727 or the metabolites thereof, the *Lactobacillus paracasei* TCI727 or the metabolites thereof can promote calcium absorption. In some embodiments, a method for improving calcium absorption of a subject in need thereof by using the *Lactobacillus paracasei* TCI727 or the metabolites thereof is provided, including administering to the subject an effective amount of a composition containing the *Lactobacillus paracasei* TCI727 or the metabolites thereof. This method can improve calcium absorption of a subject. In some embodiments, the *Lactobacillus paracasei* TCI727 or the metabolites thereof can promote calcium absorption with the help of phytase to decompose phytic acid, so as to avoid the influence of phytic acid in the daily diet on oral calcium supplementation. In addition, in some embodiments, the *Lactobacillus paracasei* TCI727 or the metabolites thereof can increase the content of calcium in bone cells and increase the content of osteocalcin in the subject. In this way, the *Lactobacillus paracasei* TCI727 or the metabolites thereof are suitable for providing safe and effective calcium-supplementing probiotics.

DETAILED DESCRIPTION

Figure 1:
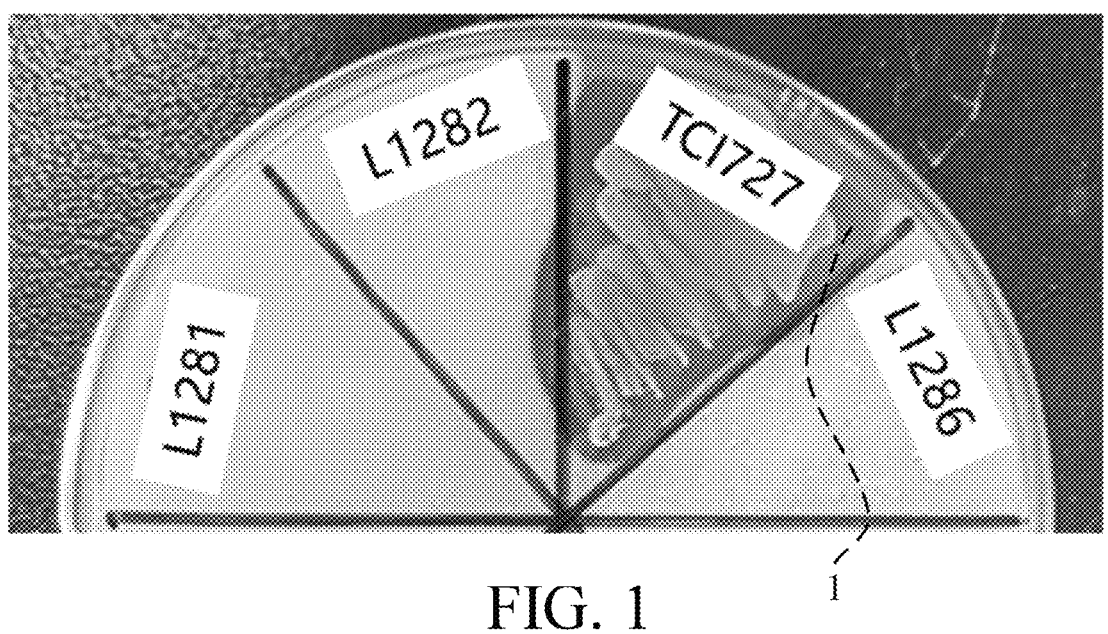
FIG. 1 is a photo showing results of activity tests on phytase with different species of *Lactobacillus paracasei* TCI727, L1281, L1282, and L1286 in a sodium phytate medium.

In order to enable a person of ordinary skill in the art to understand the characteristics of the present invention, the following general descriptions and definitions are given for the terms mentioned in the specification and the scope of the patent application. Unless otherwise specified, all technical and scientific terms used herein have the meanings as commonly understood by a person skilled in the art to the present invention. In case of conflict, the definitions in this specification shall control.

In the present invention, statistical analysis is conducted by using Excel software. Data is expressed as mean±standard deviation (SD), and the differences between groups are analyzed by student's t-test.

Herein, the term "subject" refers to a human or a non-human mammal, preferably a human.

Herein, the term "effective amount" refers to the amount of a substance required to elicit a specified effect in a subject. As known to a person skilled in the art, the effective amount will vary depending on the route of administration, the use of excipients, and the possibility of co-occurrence with other substances.

In the present invention, a novel strain was screened from raw milk (milk of cows), and the novel strain was identified as a species of *Lactobacillus paracasei* according to genetic relationship through 16S rRNA sequence analysis, and was then named *Lactobacillus paracasei* TCI727. Herein, the *Lactobacillus paracasei* TCI727 is deposited in the Food Industry Research and Development Institute with a deposit number of BCRC 911032 and the Deutsche Sammlung von Mikroorganismen und Zellkulturen GmbH (DSMZ Address: Inhoffenstr. 7 B D-38124 Braunschweig, Germany) with an accession number of DSM 33756. The deposited date of the *Lactobacillus paracasei* TCI727 in DSMZ is Jan. 7, 2021. The *Lactobacillus paracasei* TCI727 has the 16S rRNA sequence as set forth in SEQ ID NO: 1.

The *Lactobacillus paracasei* TCI727 is a gram-positive species of bacteria that can grow in an anaerobic environment, which belongs to facultative anaerobic lactic acid bacteria. The *Lactobacillus paracasei* TCI727 grows at 35-37° C., and can survive at pH 3-7.

In some embodiments, the *Lactobacillus paracasei* TCI727 or the metabolites thereof can promote calcium absorption. The promotion of calcium absorption may refer to providing an effective amount of phytase to a subject, increasing the vitamin D level in a subject, improving the vitamin D level, the content of calcium in bone cells, and the content of osteocalcin in a subject, promoting calcium absorption of a subject, promoting osteogenesis of a subject, or any combination thereof.

In some embodiments, a method for preparing the metabolites of the *Lactobacillus paracasei* TCI727 is as follows, for example, a culture medium containing the *Lactobacillus paracasei* TCI727 and the metabolites obtained through metabolic cycle of the *Lactobacillus paracasei* TCI727 may be used directly.

In some embodiments, a method for preparing the metabolites of the *Lactobacillus paracasei* TCI727 is as follows, for example, a solution containing the metabolites with solid substances such as the *Lactobacillus paracasei* TCI727 removed is used. The removal of the solid substances may be implemented by using any proper operations so long as it does not adversely affect the desired benefit of the metabolites produced after culture. Generally, the removal of the solid substances is implemented by physical means, and the physical means may be operations such as centrifugation, filtration with membrane, and precipitation and decantation. If necessary, the foregoing physical operations may be repeated or combined to remove as much as possible solid substances such as strains from the culture medium.

In some embodiments, a composition containing the *Lactobacillus paracasei* TCI727 or the metabolites thereof for promoting calcium absorption may be made into foods, drinks, nutritional supplements, or medicaments.

In some embodiments, a food composition containing the *Lactobacillus paracasei* TCI727 or the metabolites thereof for promoting calcium absorption may be a health food, food for special health use, functional food, nutritional supplement, or special nutritional food. The food composition containing the *Lactobacillus paracasei* TCI727 or the metabolites thereof for promoting calcium absorption may be made into dairy products, meat products, breads, pasta, cookies, troches, capsules, juices, teas, sports drinks, nutritional drinks, and the like, but not limited thereto.

In some embodiments, the health food, food for special health use, functional food, nutritional supplement, or special nutritional food may be consumed at different frequencies, such as once a day, multiple times a day, or once every few days, depending on the age, weight, and health status of a subject who needs the administration of the food composition. Alternatively, the content of the *Lactobacillus paracasei* TCI727 or the metabolites thereof in the health food, food for special health use, functional food, nutritional supplement, or special nutritional food in any embodiment may be adjusted according to the needs of subjects who need the administration of the food composition, for example, the content may be adjusted to the daily dose.

Example 1: Screening and Identification of *Lactobacillus paracasei* TCI727

(1-1) Screening

A proper amount of sample was taken from raw milk and plated on a solid lactobacilli MRS broth (BD Difco™ Lactobacilli MRS Broth, with 1.5 vol % of agar) plate and then cultured in an anaerobic environment (that is, the oxygen concentration in the culture environment was 1 vol %) at 37° C., to form a single colony. Herein, after culture for 16 h, the single colony was formed.

(1-2) Identification

A plurality of single colonies were picked from (1-1) and subjected to strain identification for each single colony by 16S rRNA of lactic acid bacteria. During the strain identification, the polymerase chain reaction (PCR) was carried out to obtain 16S rRNA sequences (SEQ ID NO: 1 to SEQ ID NO: 4) of these single colonies. Then, the gene sequences as set forth in SEQ ID NO: 1 to SEQ ID NO: 4 were aligned with 16S rRNA sequences of other lactobacilli strains from the website of the National Center for Biotechnology Information (NCBI), to obtain the similarity between the 16S rRNA sequences of these single colonies and the 16S rRNA sequences of other *Lactobacillus paracasei* subspecies shown in Table 1.

TABLE 1

| Strain NO. | Source of isolation | 16S rRNA sequence Sequence NO. | Similarity (Per. 1 dent) | *Lactobacillus paracasei* strain for alignment (NCBL accession number) |
|---|---|---|---|---|
| TCI727 | Raw milk (milk of cows) | SEQ ID NO: 1 | 97.05% | CP029686.1, CP026097.1, CP025582.1, AB070609.1, MT505628.1 |
| L1281 | Raw milk (milk of cows) | SEQ ID NO: 2 | 98.23-98.83% | MN480476.1, MT886394.1, MN480472.1, MT473696.1 |
| L1282 | Cow dung | SEQ ID NO: 3 | 99.71-99.81% | MH891696.1, MT463546.1, MT505636.1, MT473302.1, MT463826.1 |
| LI 286 | Human breast milk | SEQ ID NO: 4 | 99.91-100.00% | MT613486.1, MT611749.1, MG551244.1, MF632297.1, ON366855.1, ON366694.1, ON366685.1 |

The single colony with the gene sequence as set forth in SEQ ID NO: 1 isolated from raw milk and similar to other *Lactobacillus paracasei* subspecies ("*Lactobacillus paracasei* strain for alignment" shown in Table 1) by 97.05% was named *Lactobacillus paracasei* TCI727. In addition, the *Lactobacillus paracasei* TCI727 was deposited in the Food Industry Research and Development Institute with a deposit number of BCRC 911032 and the Deutsche Sammlung von Mikroorganismen und Zellkulturen GmbH (DSMZ) with a deposit number of DSM 33756.

The single colony with the gene sequence as set forth in SEQ ID NO: 2 isolated from raw milk and similar to other *Lactobacillus paracasei* subspecies ("*Lactobacillus paracasei* strain for alignment" shown in Table 1) by 98.23-98.83% was named *Lactobacillus paracasei* L1281.

The single colony with the gene sequence as set forth in SEQ ID NO: 3 isolated from cow dung and similar to other *Lactobacillus paracasei* subspecies ("*Lactobacillus paracasei* strain for alignment" shown in Table 1) by 99.71-99.81% was named *Lactobacillus paracasei* L1282.

The single colony with the gene sequence as set forth in SEQ ID NO: 4 isolated from human breast milk and similar to other *Lactobacillus paracasei* subspecies ("*Lactobacillus paracasei* strain for alignment" shown in Table 1) by 99.91-100.00% was named *Lactobacillus paracasei* L1286.

(1-3) Analysis on the Alignment of Similarity by Using the NCBI Basic Local Alignment Search Tool (BLAST):

| Strain NO. | Strain name | Strain sequence | Subspecies NO. | Similarity |
|---|---|---|---|---|
| TCI727 | *Lactobacillus paracasei* TCI727 | SEQ NO: 1 | L1281 L1282 L1286 | 98 77% 97.94% 98.16% |

Based on this, according to the alignment results in Table 2, even the same strain isolated from raw milk has different subspecies to produce different effects, and even though TCI727 and *Lactobacillus paracasei* L1281 are as high as 98.77% similar, they still cannot produce the same effect. The experimental results thereof are described in Example 4 below.

Example 2: Preparation of Bacterial Broth Containing *Lactobacillus paracasei* TCI727 or *Lactobacillus paracasei* L1281 or *Lactobacillus paracasei* L1282 or *Lactobacillus paracasei* L1286

(2-1) Materials

Culture medium: BD Difco™ Lactobacilli MRS Broth.

(2-2) Experimental Procedure

First, the *Lactobacillus paracasei* TCI727 obtained in Example 1 was used as a target strain.

The target strain was inoculated in 1 L of lactobacilli MRS broth, and the quantity of the target strain in the lactobacilli MRS broth was adjusted, to form an initial bacterial broth with an absorbance (OD600) of 0.1.

Then, the initial bacterial broth was cultured at a constant temperature 37° C. in an anaerobic environment for 24 h to form a bacterial broth of *Lactobacillus paracasei* TCI727 (a bacterial broth containing *Lactobacillus paracasei* TCI727).

The *Lactobacillus paracasei* L1281 obtained in Example 1 was used as a target strain, and a bacterial broth of *Lactobacillus paracasei* L1281 was prepared according to the same experimental procedure above.

The *Lactobacillus paracasei* L1282 obtained in Example 1 was used as a target strain, and a bacterial broth of *Lactobacillus paracasei* L1282 was prepared according to the same experimental procedure above.

The *Lactobacillus paracasei* L1286 obtained in Example 1 was used as a target strain, and a bacterial broth of *Lactobacillus paracasei* L1286 was prepared according to the same experimental procedure above.

Example 3: Preparation of Metabolites of *Lactobacillus paracasei* TCI727

The bacterial broth of *Lactobacillus paracasei* TCI727 obtained in Example 2 was centrifuged at a rotational speed of 5,000×g for 20 min by using the Thermo Megafuge 16 centrifuge to form a supernatant without *Lactobacillus paracasei* TCI727 and a precipitate containing *Lactobacillus paracasei* TCI727.

Herein, the supernatant (that is, the metabolites of *Lactobacillus paracasei* TCI727) without the strain and the precipitate containing the strain (that is, *Lactobacillus paracasei* TCI727) were obtained.

Example 4: Detection on Phytase Activity

Detection principle: The phytic acid in the medium is decomposed, so zones of clearing are observed in the medium, indicating that the strain coated on the corresponding zones has phytase activity: conversely, if the medium maintains a turbid state, then the strain coated on the corresponding zones has no phytic acid decomposing activity.

(4-1) Materials
1. Samples to be detected: The bacterial broth of *Lactobacillus paracasei* TCI727, the bacterial broth of *Lactobacillus paracasei* L1281, the bacterial broth of *Lactobacillus paracasei* L1282, and the bacterial broth of *Lactobacillus paracasei* L1286 that were obtained in Example 2 were used.
2. Culture medium containing sodium phytate (hereinafter referred to as sodium phytate medium): containing 10% (v/v) of rumen fluid (Brand: ELITE-MEDIA), 0.25% of glucose, 0.25% of cellobiose (Sigma), 0.3% of starch (Sigma), 1.8% (v/v) of agar (BD), and 1.0% (w/v) of sodium phytate (Sigma).
3. Reagent 1: containing 6.25% (w/v) of aqueous ammonium molybdate solution and 0.42% aqueous ammonium vanadate solution.

(4-2) Experimental Procedure
1. The concentrations of the bacterial broth of *Lactobacillus paracasei* TCI727, the bacterial broth of *Lactobacillus paracasei* L1281, the bacterial broth of *Lactobacillus paracasei* L1282, and the bacterial broth of *Lactobacillus paracasei* L1286 that were obtained in Example 2 were respectively normalized to OD600 nm=1.0, and then these bacterial broths were respectively coated on four zones in the sodium phytate medium and then cultured at 37° C. in an anaerobic environment for 5 days.
2. Next, 2% (w/v) of aqueous cobalt chloride solution was covered on the surface of the sodium phytate medium, standing for 5 min, and then removed.
3. Then, the reagent 1 was added and left to stand at room temperature for 5 min.
4. The reagent 1 was removed, and whether zones of clearing 1 appear in the sodium phytate medium was observed.

(4-3) Experimental Result
It can be learned from FIG. 1 that, as compared with the foggy and opaque zones (indicating that phytic acid still existed thereon) of the other three strains (that is, *Lactobacillus paracasei* L1281, *Lactobacillus paracasei* L1282, and *Lactobacillus paracasei* L1286), the zones of clearing 1 where phytic acid had been eliminated were clearly observed around the *Lactobacillus paracasei* TCI727 strain in the corresponding zones with the bacterial broth of *Lactobacillus paracasei* TCI727 coated in the sodium phytate medium, indicating that *Lactobacillus paracasei* TCI727 had phytase activities.

Therefore, the *Lactobacillus paracasei* TCI727 or the metabolites thereof was shown to decompose phytic acid with the help of phytase.

Example 5: Detection of Capability of TCI727 to Produce Vitamin D3

Experimental purpose: It is known that the active transport of calcium has to be regulated by vitamin D, so in order to test the capability of the *Lactobacillus paracasei* TCI727 of the present invention to produce vitamin D3, the vitamin D3 level in the supernatant of *Lactobacillus paracasei* TCI727 obtained in Example 3 was detected by using the ELISA kit.

(5-1) Detection of Vitamin D3 (VD3) Using ELISA Kit
Materials
Vitamin D3 ELISA detection kit (purchased from Cloud-clone corp; Cat. CEA920Ge) containing the following solutions: standard solution, standard diluent, detection reagent A, detection reagent B, assay diluent A, assay diluent B, reagent diluent, TMB substrate, stop solution, and wash buffer: its stock solution is a concentrate (30×).

Preparation Before Experiment
1. Preparation of standard serial diluted solution: A standard solution was redissolved with 1 mL of standard diluent at room temperature for 10 min to fully dissolve the standard solution, and shaken gently (with no bubbles), to obtain a redissolved standard solution with a final concentration of 200 ng/mL. 50 μL of redissolved standard solution was added in a 1.5 mL microcentrifuge tube containing 950 μL of standard diluent to make a final concentration of 1000 pg/mL for use. A standard diluent was added in 6 new 1.5 mL microcentrifuge tubes respectively by an equal volume (100 μL). Next, 100 μL of redissolved standard solution was added in a first microcentrifuge tube and mixed uniformly. Then, 100 μL of solution from the first microcentrifuge tube was added in a second microcentrifuge tube, and dilution was carried out as such sequentially until a sixth microcentrifuge tube. Finally, standard serial diluted solutions with concentrations of 500 pg/mL, 250 pg/mL, 125 pg/mL, 62.5 pg/mL, 31.25 pg/mL, and 15.625 pg/mL were obtained. In addition, only a standard diluent (0 ng/mL) was used as a control group.
2. Preparation of first control group: The preparation process was the same as that of the standard serial diluted solution.
3. The steps for preparing the detection reagent A, operation solution, detection reagent B operation solution, 1× wash buffer, and TMB substrate were performed according to the instruction manual.
4. 1×DPBS: 10×DPBS (purchased from Gibco; Cat. 14200-075) was diluted 10-fold with sterilized ddH$_2$O, pH 7.0-7.2.
5. Assay sample: from the supernatant of *Lactobacillus paracasei* TCI727 obtained in Example 3 and from the first control group obtained in (5-1). The supernatant of *Lactobacillus paracasei* TCI727 and the first control group were diluted to a proper concentration (to allow the concentration of the assay sample falls within a linear range of a standard curve). The first control group and the supernatant of *Lactobacillus paracasei* TCI727 were diluted respectively with 1×DPBS in a proper ratio. The diluted supernatant of *Lactobacillus paracasei* TCI727 was used as an experimental group (without cells). The diluted first control group was used as a blank group (without cells). The control group and the experimental group were both used in the subsequent step of detecting vitamin D3.

The following is a brief description of the step of detecting vitamin D3. The detailed operation steps may be performed by referring to the instruction manual attached to the vitamin D3 detection reagent kit.

Experimental Procedure
1. 50 μL/well of standard serial diluted solution (in the foregoing concentrations), control group, and experimental group were added in a 96-well plate (pre-coated with an anti-vitamin D3 monoclonal antibody with mono-specificity and ready to use, and included in the vitamin D3 detection reagent kit), and then 50 μL/well of detection reagent A operation solution was added immediately to obtain a mixture. The mixture was shaken gently for mixing and underwent reaction at 37° C. for 1 h to form an acted solution.
2. The acted solution was aspirated from the plate, and then 350 μL/well of 1× wash buffer was added and left to stand for 1-2 min. After that, the plate was turned upside down and placed on a paper towel to remove as much liquid as possible from the wells.
3. Then, 100 μL/well of detection reagent B operation solution was added into the wells to react at 37° C. for 30 min.
4. The operation process in step 2 was repeated for 5 times.
5. 90 μL/well of TMB substrate was added into the wells to react in the dark at 37° C. for 10 min. This step needs to be performed in the dark and react for no more than 30 min.
6. 50 μL/well of stop solution was added into the wells, and then the plate was tapped to mix well (until the color changed).
7. Finally, the absorbance at O.D. 450 nm of each well was measured with a spectrometer (Thermo Fisher Scientific), and the absorbance of each well was compared with the absorbance of the standard serial diluted solution to calculate the concentration of vitamin D3 of the assay sample (the supernatant in each group).

(5-2) Experimental Result

Figure 2:
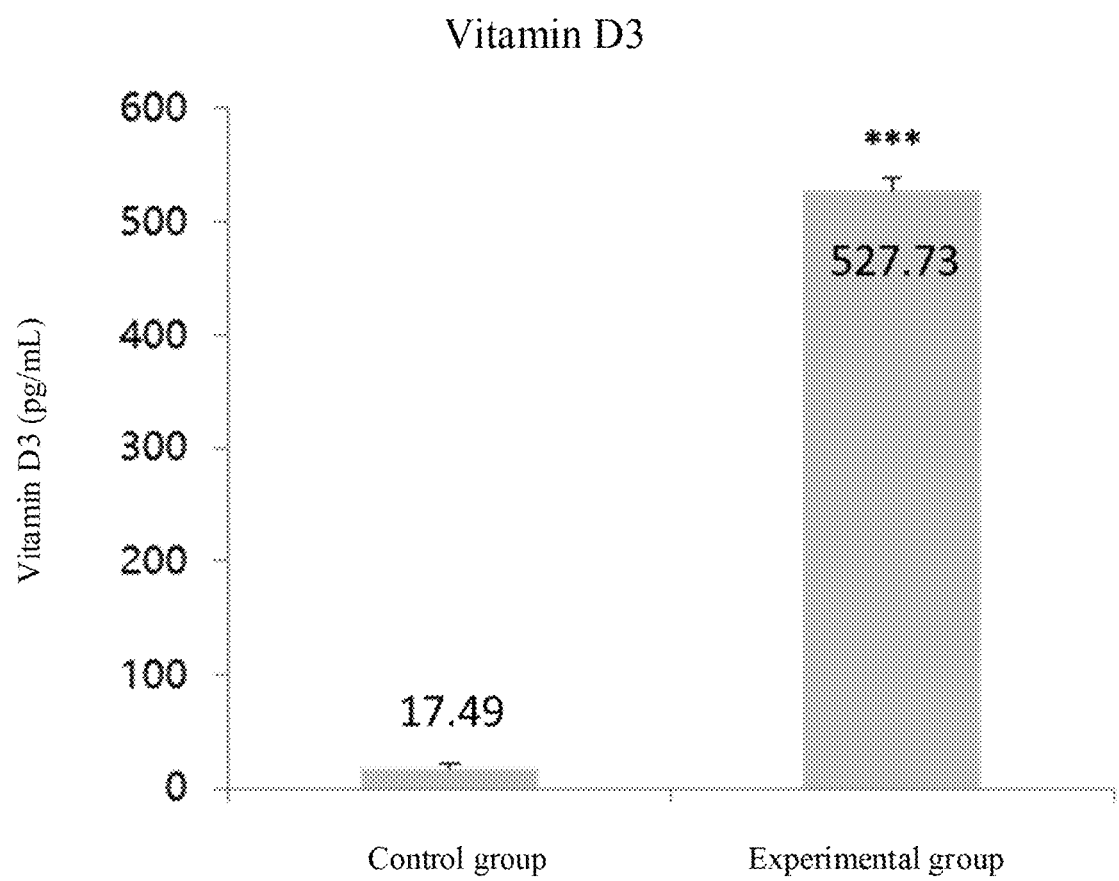
FIG. 2 is a histogram of the vitamin D3 level in the *Lactobacillus paracasei* TCI727 shown in FIG. 1.

Refer to FIG. 2. The vitamin D3 level measured in the control group was 17.49 pg/mL, and the vitamin D3 level measured in the experimental group was 527.73 pg/mL. In other words, as compared with the control group, the experimental group obtained through the treatment of the supernatant of *Lactobacillus paracasei* TCI727 had the vitamin D3 level significantly increased, 30 times that of the control group (***: there is a significant difference from the control group ($p<0.001$)).

It can be learned that *Lactobacillus paracasei* TCI727 was shown to synthesize vitamin D3 autogenously and significantly increase the vitamin D3 level in the supernatant. It had been confirmed in the literature that vitamin D3 helped regulate the production of transport protein for calcium ions and enhance the activity of calcium ion pumps, thereby promoting calcium absorption in intestinal cells.

Example 6: Detection on Capability of Increasing the Content of Bone Calcium (6-1) Materials
1. Cell strain: mouse bone marrow stromal cells (hereinafter referred to as OP9 cells) of the OP9 cell strain (ATCC® CRL-2749™) purchased from the American Type Culture Collection (ATCC®).
2. Cell culture medium: containing 90% of minimum essential medium alpha medium (MEMAM, purchased from Gibco, Cat. 12000-022), 20% of fetal bovine serum (FBS, purchased from Gibco, Cat. 10437-028), and 1% of penicillin-streptomycin (purchased from Gibco, Cat. 15240-062).
3. Differentiation medium: containing 90% of Dulbecco's modified Eagle's medium (DMEM, purchased from Gibco, Cat. 12100-038) with 10% of FBS (purchased from Gibco, 10438-026) and 1% of penicillin-streptomycin (purchased from Gibco, Cat. 15140122), 50 μM of ascorbic acid (purchased from Sigma), $10^{-7}$ M of dexamethasone (purchased from Sigma), and 10 mM of β-glycerol (purchased from Sigma) added.
4. Test sample: from the supernatant of *Lactobacillus paracasei* TCI727 obtained in Example 3.
5. Dye: Alizarin Red S (purchased from Sigma) (hereinafter referred to as Alizarin Red S 2).
6. 4% of formaldehyde: purchased from ECHO, Cat. 119690010.
7. Phosphate buffered saline (PBS) solution: purchased from Gibco, product No. 10437-028.
8. $ddH_2O$.
9. CPC buffer: a trisodium phosphate solution containing 10 vol % of cetylpyridinium chloride (CPC) and 10 mM of trisodium phosphate.

(6-2) Experimental Procedure

Induction into Osteocytes
1. The OP9 cells were inoculated into a 24-well culture plate containing 500 μL of cell culture medium per well in a density of $2×10^4$ cells per well, and then cultured in a thermostatic incubator at 37° C. with a carbon dioxide concentration of 5 vol % overnight. Then, the cell culture medium was replaced with a fresh differentiation medium.
2. During the culture for 7 days, the differentiation medium was replaced with a fresh one every three days.
3. The morphological features of the cells were observed to ensure that the OP9 cells had differentiated into osteocytes, and the osteocytes were divided into a control group and an experimental group and cultured for 7 days with the differentiation medium replaced with a fresh one every three days. The differentiation medium of the experimental group contained the test sample from the supernatant of *Lactobacillus paracasei* TCI727 obtained in Example 3. The control group was a pure differentiation medium with no test sample added.
4. After the 7-day culture was completed, the cells were stained with Alizarin Red S 2.

Stain with Alizarin Red S 2 to confirm calcium precipitation
1. The differentiation medium was carefully aspirated from each well, and the osteocytes were washed with the PBS solution.
2. The PBS solution was carefully aspirated, and 4% of formaldehyde was added in each well to immobilize the osteocytes for 10 min.
3. 4% of formaldehyde was washed with $ddH_2O$.
4. An Alizarin Red S solution was prepared. 2 g of Alizarin Red S powder was dissolved in 100 mL of $ddH_2O$ and filtered using a membrane with a pore size of 0.22 μm to form the filtered Alizarin Red S solution. 100-200 μL of filtered Alizarin Red S solution was added into each well to stain for 1 min.
5. The filtered Alizarin Red S solution was carefully aspirated from each well, and the cells were washed with $ddH_2O$ for destaining. In this step, the stained sample was obtained.
6. Then, the sample was placed under a microscope to observe calcium precipitation from the osteocytes in the stained sample. Calcium precipitates in the area stained by Alizarin Red S 2.
7. 200 μL of CPC buffer was added into the stained sample and the sample was placed in a shaker to shake gently for 1 h to obtain a stained sample containing the CPC buffer.
8. 100 μL of the stained sample containing the CPC buffer in each group was added in a 96-well plate, and the absorbance at O.D. 550 nm was measured to quantitatively analyze the content of calcium in the osteocytes.

(6-3) Experimental Result

Figure 3A:
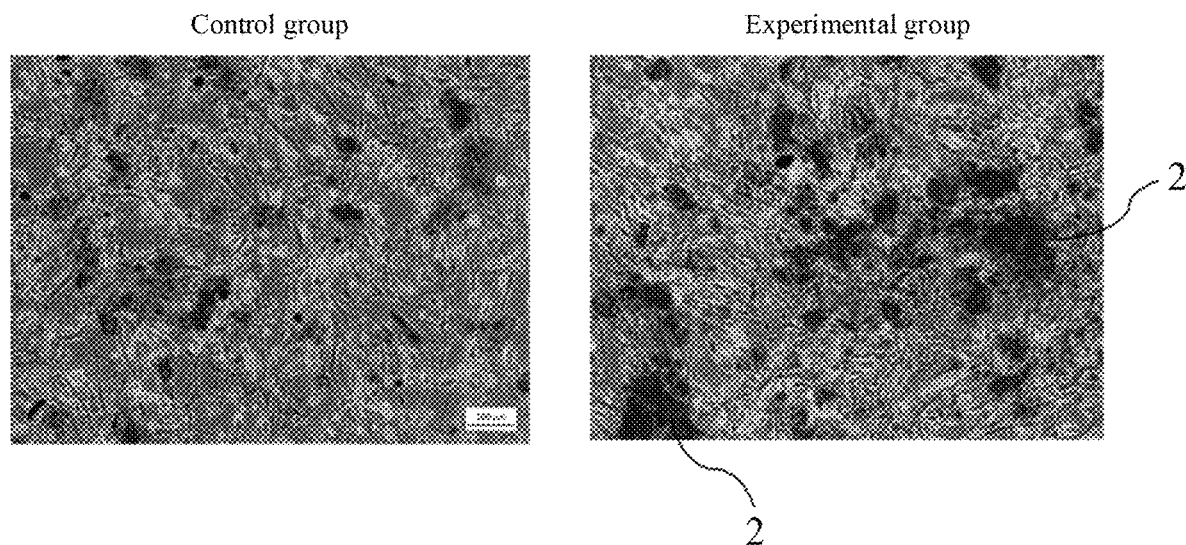
FIG. 3A is an image showing results of calcium precipitation staining in cells stained by Alizarin Red S to observe calcium precipitation in a cell experiment.

Refer to FIG. 3A. The calcium precipitation results of the control group and the experimental group were observed under a microscope. It could be seen from the staining results of osteocytes shown in FIG. 3A that as compared with the control group, the experimental group had a larger total area stained by Alizarin Red S 2.

Figure 3B:
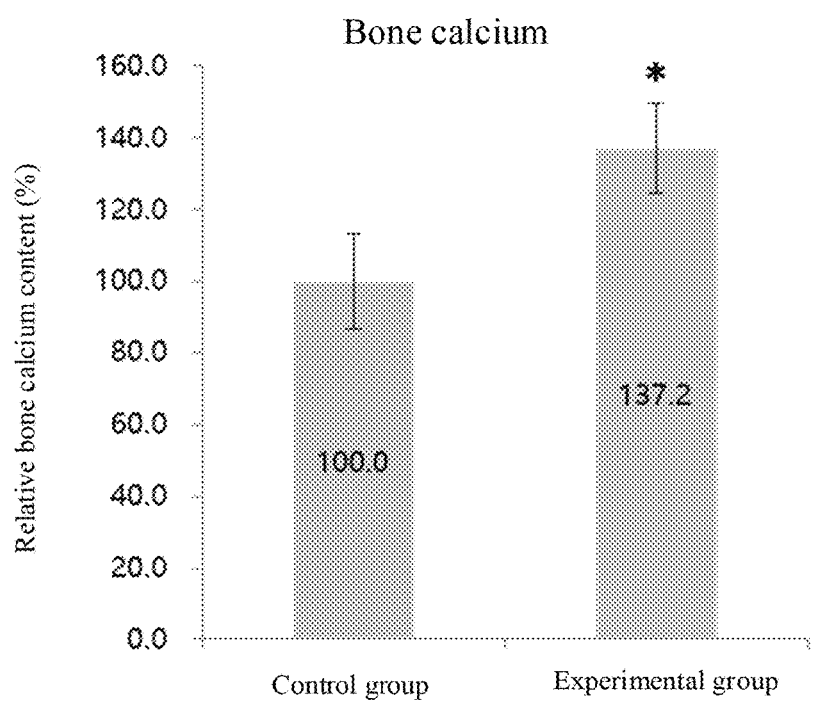
FIG. 3B is a histogram of the relative bone calcium content obtained through further quantitative statistics based on the results of calcium precipitation staining in cells shown in FIG. 3A in a cell experiment.

Based on the absorbance at O.D. 550 nm, the results of the relative bone calcium content obtained through quantitative statistics were shown in FIG. 3B. The control group was obtained without the treatment of the supernatant of *Lactobacillus paracasei* TCI727, which was regarded as producing 100% calcium precipitation by the osteocytes under normal physiological metabolism in the control group. As compared with the control group, the osteocytes in the experimental group were treated with the supernatant of *Lactobacillus paracasei* TCI727 for 7 days, and produced 137.2% calcium precipitation (*: there was a significant difference from the control group ($p<0.05$)). It can be learned that the supernatant of *Lactobacillus paracasei* TCI727 was shown to significantly increase the content of calcium in osteocytes within 7 days.

Example 7: Human Subject Experiments

In order to evaluate the capability of the *Lactobacillus paracasei* TCI727 sample to promote calcium absorption of a subject and further evaluate its capability for bone health care of a subject, human subject experiments were carried out to confirm the effect of taking *Lactobacillus paracasei* TCI727 on the calcium absorption and osteogenesis of a subject.

Experimental Design

The experiment included a control group and an experimental group with 3 subjects in each group, a total of 6 subjects. Conditions of the subjects in each group included: high risk of osteoporosis (menopausal women and/or aged >60), low bone density detected and determined by doctors, or frequent coffee drinker.

Control group: The subjects took a test sample once a day for 4 weeks. In addition, the content of calcium in blood and the content of osteocalcin in blood were measured respectively before the experiment (that is, before taking the test sample, regarded as week 0) and after the experiment (that is, after taking the test sample for 4 weeks, regarded as week 4). In the control group, the test sample took by the subjects was a simple calcium supplement. The calcium supplement (commercially available) was calcium phosphate plus calcium citrate with a dose of 500 mg/day.

Experimental group: The subjects took a test sample once a day for 4 weeks. In addition, the content of calcium in blood and the content of osteocalcin in blood were measured respectively before the experiment (that is, before taking the test sample, regarded as week 0) and after the experiment (that is, after taking the test sample for 4 weeks, regarded as week 4). In the experimental group, the test sample took by the subjects was a calcium supplement with *Lactobacillus paracasei* TCI727 strain (powder). The calcium supplement (commercially available) was calcium phosphate plus calcium citrate with a dose of 500 mg/day. The dose of the *Lactobacillus paracasei* TCI727 strain (in the form of composition to promote calcium absorption) was 50 mg/day. The *Lactobacillus paracasei* TCI727 strain was obtained in Example 3.

The content of calcium in blood and the content of osteocalcin in blood were measured by LEZEN Lab. from a blood specimen collected through venipuncture.

Figure 4A:
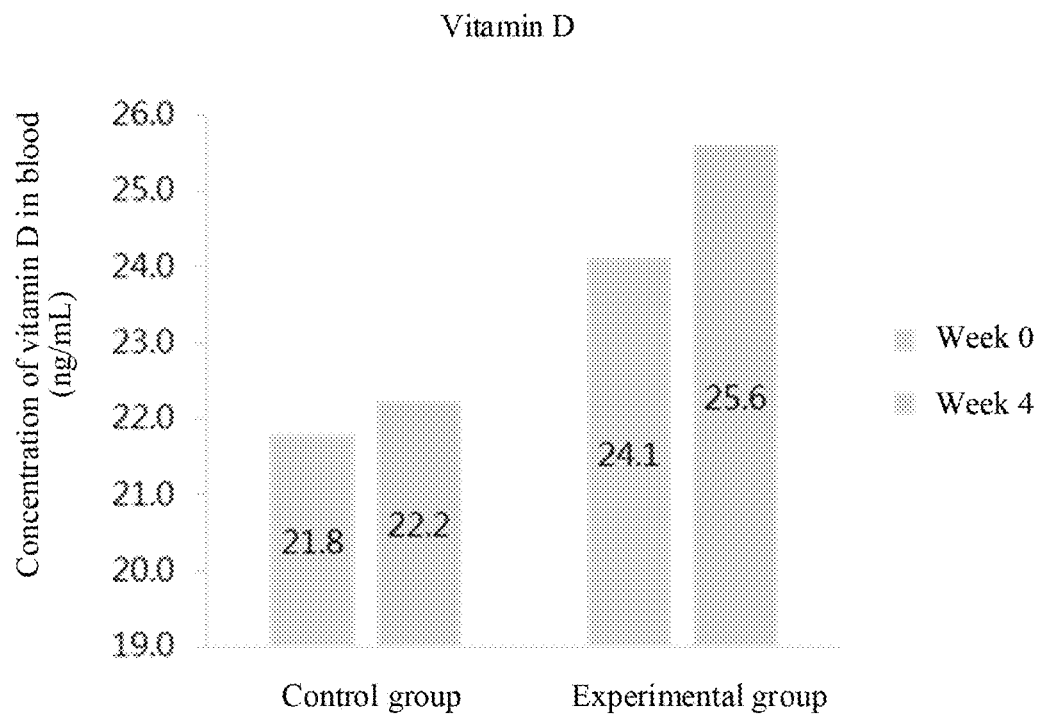
FIG. 4A is a histogram of the vitamin D level in blood detected at week 0 and week 4 in a human subject experiment.

7-1 *Lactobacillus paracasei* TCI727 Promotes the Capability of Calcium Absorption of the Subject, Thereby Increasing the Concentration of Vitamin D in Blood of the Subject Detection Results Refer to FIG. 4A. In the control group, before the experiment (week 0 in FIG. 4A), an average concentration of vitamin D in blood of the 3 subjects was 21.8 ng/mL, and after the experiment (week 4 in FIG. 4A), an average concentration of vitamin D in blood of the 3 subjects was 22.2 ng/mL. In other words, in the control group, after the subjects took the test sample of the simple calcium supplement once a day for 4 weeks, the average concentration of vitamin D in blood was only increased by 1.8%.

Correspondingly, in the experimental group, before the experiment (week 0 in FIG. 4A), an average concentration of vitamin D in blood of the 3 subjects was 24.1 ng/mL, and after the experiment (week 4 in FIG. 4A), an average concentration of vitamin D in blood of the 3 subjects was 25.6 ng/mL. In other words, in the experimental group, after the subjects took the test sample of the calcium supplement with the *Lactobacillus paracasei* TCI727 strain once a day for 4 weeks, the average concentration of vitamin D in blood was greatly increased by 6.2%. Based on this, *Lactobacillus paracasei* TCI727 was shown to synthesize vitamin D autogenously to help calcium absorption of the subject, thereby increasing the concentration of vitamin D in blood of the subject and strengthening bones.

7-2: *Lactobacillus paracasei* TCI727 Increases the Concentration of Osteocalcin in Blood of the Subject, Thereby Promoting the Capability of Osteogenesis of the Subject Studies have shown that osteocalcin is mainly produced by osteoblasts, and its content is positively correlated with osteogenesis, so osteocalcin can be used as a biological indicator of osteogenesis.

Detection Results

Figure 4B:
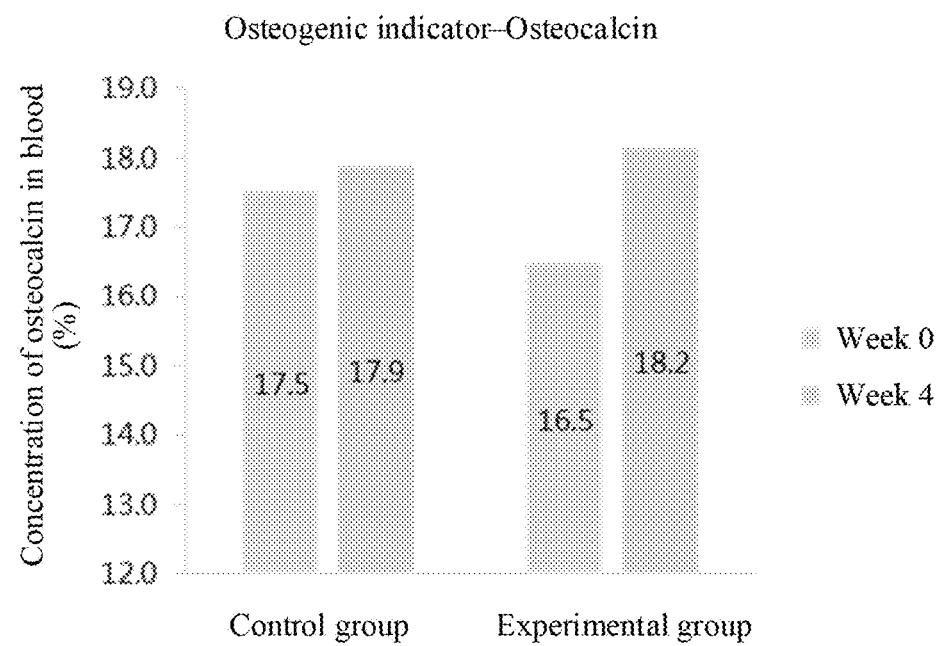
FIG. 4B is a histogram of the content of osteocalcin in blood detected at week 0 and week 4 in a human subject experiment.

Refer to FIG. 4B. In the control group, before the experiment (week 0 in FIG. 4B), an average concentration of osteocalcin in blood of the 3 subjects was 17.5%, and after the experiment (week 4 in FIG. 4B), an average concentration of osteocalcin in blood of the 3 subjects was 17.9%. In other words, in the control group, after the subjects took the test sample of the simple calcium supplement once a day for 4 weeks, the average concentration of osteocalcin in blood was only increased by 2.3%.

Correspondingly, in the experimental group, before the experiment (week 0 in FIG. 4B), an average concentration of osteocalcin in blood of the 3 subjects was 16.5%, and after the experiment (week 4 in FIG. 4B), an average concentration of osteocalcin in blood of the 3 subjects was 18.2%. In other words, in the experimental group, after the subjects took the test sample of the calcium supplement with the *Lactobacillus paracasei* TCI727 strain once a day for 4 weeks, the average concentration of osteocalcin in blood was greatly increased by 10.3%. Based on this, it was verified that the combination of calcium supplement with *Lactobacillus paracasei* TCI727 strain (powder) was shown to promote osteogenesis with a better effect than the simple calcium supplement.

Based on the above, the results of the human subject experiments had verified the capability of *Lactobacillus paracasei* TCI727 (calcium absorption-promoting strain TCI727) for bone health care.

In conclusion, according to the *Lactobacillus paracasei* in any embodiment and the use of the *Lactobacillus paracasei* TCI727 or the metabolites thereof, the *Lactobacillus paracasei* TCI727 or the metabolites thereof can promote calcium absorption. In some embodiments, a method for improving calcium absorption of a subject in need thereof by using the *Lactobacillus paracasei* TCI727 or the metabolites thereof is provided, including administering to the subject an effective amount of a composition containing the *Lactobacillus paracasei* TCI727 or the metabolites thereof. This method can improve calcium absorption of a subject. In some embodiments, the *Lactobacillus paracasei* TCI727 or the metabolites thereof can promote calcium absorption with the help of phytase to decompose phytic acid, so as to avoid the influence of phytic acid in the daily diet on oral calcium supplementation. In some embodiments, the *Lactobacillus paracasei* TCI727 or the metabolites thereof can increase the vitamin O3 level in intestinal cells. In addition, in some embodiments, the *Lactobacillus paracasei* TCI727 or the metabolites thereof can increase the content of calcium in bone cells. In some embodiments, the *Lactobacillus paracasei* TCI727 or the metabolites thereof can increase the concentration of vitamin D and the content of osteocalcin in the subject. The *Lactobacillus paracasei* TCI727 or the metabolites thereof can be used to prepare a composition for promoting calcium absorption. The composition is in a dosage form of powder, granule, tablet, liquid, or capsule. The composition containing the *Lactobacillus paracasei* TCI727 or the metabolites thereof for promoting calcium absorption can be made into a food, drink, nutritional supplement, or medicament. The composition is administrated to a subject orally.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A composition for improving calcium absorption, comprising *Lactobacillus paracasei* TCI727 and/or metabolites thereof, wherein the *Lactobacillus paracasei* TCI727 is deposited in the Deutsche Sammlung von Mikroorganismen und Zellkulturen GmbH (DSMZ) with an accession number of DSM 33756, the *Lactobacillus paracasei* TCI727 comprises a full length nucleotide sequence as set forth in SEQ ID NO:1, and the metabolites are obtained by cultivating *Lactobacillus paracasei* TCI727 in a culture broth.

2. The composition according to claim 1, comprising a phytase.

3. A method for improving calcium absorption of a subject in need thereof, comprising administering to the subject an effective amount of a composition comprising *Lactobacillus paracasei* TCI727 and/or metabolites thereof, wherein the *Lactobacillus paracasei* TCI727 is deposited in the Deutsche Sammlung von Mikroorganismen und Zellkulturen GmbH (DSMZ) with an accession number of DSM 33756, the *Lactobacillus paracasei* TCI727 comprises a full length nucleotide sequence as set forth in SEQ ID NO: 1, and the metabolites are obtained by cultivating the *Lactobacillus paracasei* TCI727 in a culture broth.

4. The method according to claim 3, wherein the *Lactobacillus paracasei* TCI727 has phytase activity, thereby achieving the effect of improving calcium absorption of the subject.

5. The method according to claim 3, wherein the *Lactobacillus paracasei* TCI727 or the metabolites thereof are used to increase a vitamin D level of the subject.

6. The method according to claim 3, wherein the *Lactobacillus paracasei* TCI727 or the metabolites thereof are used to increase a content of calcium in bone cells of the subject.

7. The method according to claim 3, wherein the *Lactobacillus paracasei* TCI727 or the metabolites thereof are used to promote calcium absorption and/or osteogenesis of the subject.

8. The method according to claim 3, wherein an effective amount of the *Lactobacillus paracasei* TCI727 in the composition is at least $1 \times 10^8$ CFU/day.

9. The method according to claim 3, wherein a dosage form of the composition is powder, granule, tablet, liquid, or colloid.

\* \* \* \* \*

SEQUENCE LISTING

```
Sequence total quantity: 4
SEQ ID NO: 1            moltype = DNA   length = 1211
FEATURE                 Location/Qualifiers
source                  1..1211
                        mol_type = genomic DNA
                        organism = Lactobacillus paracasei
SEQUENCE: 1
aattgggaag ggatacataa tacatgcaag tcgaacgagt gtactcgttg atgatcggtg   60
cttgcaccga gattcaacat ggaacgagtg gcggacgggt gagtaacacg tgggtaacct  120
gcccttaagt gggggataac atttggaaac agatgctaat accgcataga tccaagaacc  180
gcatggttct tggctgaaag atggcgtaag ctatcgcttt tggatggacc cgcggcgtat  240
tagctagttg gtgaggtaat ggctcaccaa ggcgatgata cgtagccgaa ctgagaggtt  300
gatcggccac attgggactg agacacggcc caaactccta cgggaggcag cagtagggaa  360
tcttccacaa tggacgcaag tctgatggag caacgccgcg tgagtgaaga aggctttcgg  420
gtcgtaaaac tctgttgttg gagaagaatg gtcggcagag taactgttgt cggcgtgacg  480
gtatccaacc agaaagccac ggctaactac gtgccagcag ccgcggtaat acgtaggtgg  540
caagcgttat ccggatttat tgggcgtaaa gcgagcgcag gcggttttt  aagtctgatg  600
tgaaagccct cggcttaacc gaggaagcgc atcggaaact gggaaacttg agtgcagaag  660
aggacagtgg aactccatgt gtagcggtga aatgcgtaga tatatggaag aacaccagtg  720
gcgaaggcgg ctgtctggtc tgtaactgac gctgagctcg aaagcatggg tagcgaacag  780
gattagatac cctggtagtc catgccgtaa acgatgaatg ctaggtgttg gagggtttcc  840
gcccttcagt gccgcagcta acgcattaag cattccgcct ggggagtacg accgcaaggt  900
tgaaactcaa ggaattgacg gggcccgcac aagcggtgga gcatggtggt ttaattcgaa  960
gcaacgcgaa gaccttacca gtcttgacat cttttgatcc acctgaaaag atcagtttcc 1020
ccttcggggc aattgacgtg tgcatggttg tcgtcagcct cgtgtctgaa atgttggtta 1080
gttcccgcca acgaggcaac cttatggact agttgcaagc attagttgac atctaataag 1140
actgcggtga caccgagtag tgatagccat ctcattgcct ttagacctgc ctcacacggt 1200
gctcaatgta g                                                      1211

SEQ ID NO: 2            moltype = DNA   length = 1145
FEATURE                 Location/Qualifiers
source                  1..1145
                        mol_type = genomic DNA
                        organism = Lactobacillus paracasei
SEQUENCE: 2
ccaaattttt tgtgcagcaa tagacggctc gctccctaaa agggttacgc caccggcttc   60
gggtgttaca aactctcatg gtgtgacggg cggtgtgtac aaggcccggg aacgtattca  120
ccgcggcgtg ctgatccgcg attactagcg attccgactt cgtgtaggcg agttgcagcc  180
tacagtccga actgagaatg gctttaagag attagcttga cctcgcggtc tcgcaactcg  240
ttgtaccatc cattgtagca cgtgtgtagc ccaggtcata aggggcatga tgatttgacg  300
tcatcccccac cttcctccgg tttgtcaccg gcagtcttac tagagtgccc aactaaatgc  360
tggcaactag tcataagggt tgcgctcgtt gcgggactta acccaacatc tcacgacacg  420
agctgacgac aaccatgcac cacctgtcat tttgccccgg aagggggaaac ctgatctctc  480
aggtgatcaa aagatgtcaa gacctggtaa ggttcttcgc gttgcttcga attaaaccaa  540
tgctccaccg cttgtgcggg ccccgtcaa ttccttttgag tttcaacctt gcggtcgtac  600
tccccaggcg gaatgcttaa tgcgttagct gcggcactga agggcggaaa ccctccaaca  660
cctagcattc atcgtttacg gcatggacta ccagggtatc taatcctgtt cgctacccat  720
gctttcgagc ctcagcgtca gttacagacc agacagccgc cttcgccact ggtgttcttc  780
catatatcta cgcatttcac cgctacacat ggagttccac tgtcctcttc tgcactcaag  840
tttcccagtt tccgatgcgc ttcctcggtt aagccgaggg ctttcacatc agacttaaaa  900
aaccgcctgc gctcgcttta cgcccaataa atccggata acgcttgcca cctacgtatt  960
accgcggctg ctggcacgta gttagccgtg gctttctggt tggataccgt cacgccgaca 1020
cagttactct gccgaccatt ctctcacaca gagtttacga cccgaagctc tcactcacgc 1080
ggcgtgctcc atcagactgc gtcattgtgg aagatctact gtcttcctgt ggggagagag 1140
```

```
caccc                                                                  1145

SEQ ID NO: 3            moltype = DNA  length = 1033
FEATURE                 Location/Qualifiers
source                  1..1033
                        mol_type = genomic DNA
                        organism = Lactobacillus paracasei
SEQUENCE: 3
ccaaactttt gtcaccttag acggctcgct ccctaaaagg gttacgccac cggcttcggg    60
tgttacaaac tctcatggtg tgacgggcgg tgtgtacaag gcccgggaac gtattcaccg   120
cggcgtgctg atccgcgatt actagcgatt ccgacttcgt gtaggcgagt tgcagcctac   180
agtccgaact gagaatggct ttaagagatt agcttgacct cgcggtctcg caactcgttg   240
taccatccat tgtagcacgt gtgtagccca ggtcataagg ggcatgatga tttgacgtca   300
tcccaccctt cctccggttt gtcaccggca gtcttactag agtgcccaac taaatgctgg   360
caactagtca taagggttgc gctcgttgcg ggacttaacc caacatctca cgacacgagc   420
tgacgacaac catgcaccac ctgtcatttt gcccccgaag gggaaacctg atctctcagg   480
tgatcaaaag atgtcaagac ctggtaaggt tcttcgcgtt gcttcgaatt aaaccacatg   540
ctccaccgct tgtgcgggcc cccgtcaatt cctttgagtt tcaaccttgc ggtcgtactc   600
cccaggcgga atgcttaatg cgttagctgc ggcactgaag ggcggaaacc ctccaacacc   660
tagcattcat cgtttacggc atggactacc agggtatcta atcctgttcg ctacccatgc   720
tttcgagtct cagcgtcagt tacagaccag acagccgcct tcgccactgg tgttcttcca   780
tatatctacg catttcaccg ctacacatgg agttccactg tcctcttctg cactcaagtt   840
tcccagtttc cgatgcgctt cctcggttaa gccgagggct ttcacatcag acttaaaaaa   900
ccgcctgcgc tcgctttacg cccaataaat ccggataacg cttgccacct acgtattacc   960
gcggctgctg gcacgtagtt agccgtggct ttctggttgg ataccgtcac gccgacacag  1020
ttactctgcc gac                                                     1033

SEQ ID NO: 4            moltype = DNA  length = 1072
FEATURE                 Location/Qualifiers
source                  1..1072
                        mol_type = genomic DNA
                        organism = Lactobacillus paracasei
SEQUENCE: 4
cgggcttctg ctccaggaat aaacggctcg ctccctaaaa gggttacgcc accggcttcg    60
ggtgttacaa actctcatgg tgtgacgggc ggtgtgtaca aggcccggga acgtattcac   120
cgcggcgtgc tgatccgcga ttactagcga ttccgacttc gtgtaggcga gttgcagcct   180
acagtccgaa ctgagaatgg ctttaagaga ttagcttgac ctcgcggtct cgcaactcgt   240
tgtaccatcc attgtagcac gtgtgtagcc caggtcataa ggggcatgat gatttgacgt   300
catcccacc ttcctccggt ttgtcaccgg cagtcttact agagtgccca actaaatgct   360
ggcaactagt cataagggtt gcgctcgttg cgggacttaa cccaacatct cacgacacga   420
gctgacgaca accatgcacc acctgtcatt ttgccccga aggggaaacc tgatctctca   480
ggtgatcaaa agatgtcaag acctggtaag gttcttcgcg ttgcttcgaa ttaaaccaca   540
tgctccaccg cttgtgcggg ccccgtcaa ttcctttgag tttcaacctt gcggtcgtac   600
tccccaggcg gaatgcttaa tgcgttagct gcggcactga agggcggaaa ccctccaaca   660
cctagcattc atcgtttacg gcatggacta ccagggtatc taatcctgtt cgctacccat   720
gctttcgagc ctcagcgtca gttacagacc agacagccgc cttcgccact ggtgttcttc   780
catatatcta cgcatttcac cgctacacat ggagttccac tgtcctcttc tgcactcaag   840
tttcccagtt tccgatgcgc ttcctcggtt aagccgaggg cttttcacatc agacttaaaa   900
aaccgcctgc gctcgcttta cgcccaataa atccggataa cgcttgccac ctacgtatta   960
ccgcggctgc tggcacgtag ttagccgtgg ctttctggtt ggataccgtc acgccgacaa  1020
cagttactct gccgaccatt cttctccaac aacagagttt tacgacccga aa          1072
```